United States Patent
Wei et al.

(10) Patent No.: US 9,972,081 B2
(45) Date of Patent: May 15, 2018

(54) METHOD AND SYSTEM FOR ESTIMATING A DEFLATED LUNG SHAPE FOR VIDEO ASSISTED THORACIC SURGERY

(71) Applicant: EDDA TECHNOLOGY, INC., Princeton, NJ (US)

(72) Inventors: Guo-Qing Wei, Plainsboro, NJ (US); Li Fan, Belle Mead, NJ (US); Cheng-Chung Liang, West Windsor, NJ (US); Jianzhong Qian, Princeton Junction, NJ (US); Xiaolan Zeng, Princeton, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 0 days. days.

(21) Appl. No.: 14/926,480

(22) Filed: Oct. 29, 2015

(65) Prior Publication Data

US 2016/0128782 A1 May 12, 2016

Related U.S. Application Data

(60) Provisional application No. 62/072,685, filed on Oct. 30, 2014.

(51) Int. Cl.
*G06T 7/00* (2017.01)
*A61B 19/00* (2006.01)
(Continued)

(52) U.S. Cl.
CPC .............. *G06T 7/001* (2013.01); *A61B 5/091* (2013.01); *A61B 19/46* (2013.01); *A61B 19/50* (2013.01);
(Continued)

(58) Field of Classification Search
CPC ......... G06T 7/001; G06T 17/20; G06T 19/00; A61B 5/091; A61B 6/032; A61B 19/46; A61B 19/50; A61B 19/5225
See application file for complete search history.

(56) References Cited

U.S. PATENT DOCUMENTS 8,483,831 B1 * 7/2013 Hlavka ................. A61B 18/08
600/529
2004/0092811 A1 * 5/2004 Hill ........................ A61B 6/032
600/413
(Continued)

OTHER PUBLICATIONS

International Search Report and Written Opinion dated Mar. 2, 2016 in International Application PCT/US2015/058433.
(Continued)

*Primary Examiner* — Jingge Wu
(74) *Attorney, Agent, or Firm* — Pillsbury Winthrop Shaw Pittman LLP

(57) ABSTRACT

The present teaching relates to surgical procedure assistance. In one example, a first volume of air inside a lung is obtained based on a first image of the lung captured prior to a surgical procedure. The lung has a first shape on the first image. A second volume of air deflated from the lung is determined based on a second image of the lung captured during the surgical procedure. A second shape of the lung is estimated based on the first shape of the lung and the first air volume inside the lung and second volume of air deflated from the lung. A surgical plan is updated based on the estimated second shape of the lung.

21 Claims, 6 Drawing Sheets

(51) Int. Cl.
  *A61B 5/091* (2006.01)
  *G06T 17/20* (2006.01)
  *G06T 19/00* (2011.01)
  *A61B 6/03* (2006.01)

(52) U.S. Cl.
  CPC .......... *A61B 19/5225* (2013.01); *G06T 17/20* (2013.01); *G06T 19/00* (2013.01); *A61B 6/032* (2013.01); *A61B 2019/461* (2013.01); *A61B 2019/463* (2013.01); *G06T 2210/41* (2013.01)

(56) References Cited

U.S. PATENT DOCUMENTS

| | | | |
|---|---|---|---|
| 2008/0114551 A1* | 5/2008 | Roecker | A61B 5/091 702/24 |
| 2008/0183073 A1* | 7/2008 | Higgins | G06T 19/003 600/425 |
| 2011/0060215 A1* | 3/2011 | Tupin, Jr. | A61B 5/0507 600/425 |
| 2011/0093243 A1* | 4/2011 | Tawhai | G06F 17/5018 703/2 |
| 2011/0237897 A1* | 9/2011 | Gilboa | A61B 1/00154 600/202 |
| 2011/0286574 A1* | 11/2011 | Suzuki | A61B 6/032 378/8 |
| 2012/0215504 A1* | 8/2012 | Parker | A61B 5/083 703/2 |
| 2012/0219200 A1 | 8/2012 | Reeves et al. | |
| 2012/0288173 A1 | 11/2012 | Rai et al. | |
| 2012/0289825 A1* | 11/2012 | Rai | A61B 6/463 600/425 |
| 2013/0303932 A1* | 11/2013 | Helfenbein | A61B 5/091 600/538 |
| 2014/0376789 A1* | 12/2014 | Xu | G06T 5/003 382/128 |
| 2015/0005659 A1* | 1/2015 | Masumoto | A61B 6/032 600/538 |
| 2016/0236009 A1* | 8/2016 | Sabczynski | A61B 5/103 |
| 2017/0020628 A1* | 1/2017 | Averbuch | A61B 34/10 |

OTHER PUBLICATIONS

Ng, CSH et al., Video assisted thoracic surgery in the management of spontaneous pneumothorax: the current status, Postgrad Medical Journal, Mar. 2006, vol. 82, No. 965, pp. 179-185.

Choi, S. et al., Improved CT based estimate of pulmonary gas trapping accounting for scanner and lung volume variations in a mulitcenter asthmatic study, Journal of Applied Physiology, Aug. 7, 2014, vol. 117, No. 6, pp. 593-603.

Dubois, AB et al., A new method for measuring airway resistance in man using a body plethysmograph: values in normal subjects and in patients with respiratory disease, Journal of Clinical Investigation, Oct. 17, 1955, vol. 35, No. 3, pp. 327-335.

Plathrow, C. et al., Quantification of lung tumor volume and rotation at 3D dynamic parallel MR imaging with view sharing: preliminary results, Radiology, Jun. 26, 2006, vol. 240, No. 2, pp. 537-545.

International Preliminary Report on Patentability dated May 11, 2017 in International Application PCT/US2015/058433.

* cited by examiner

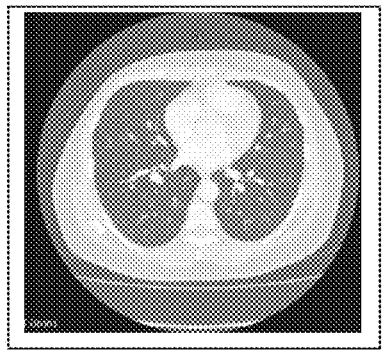 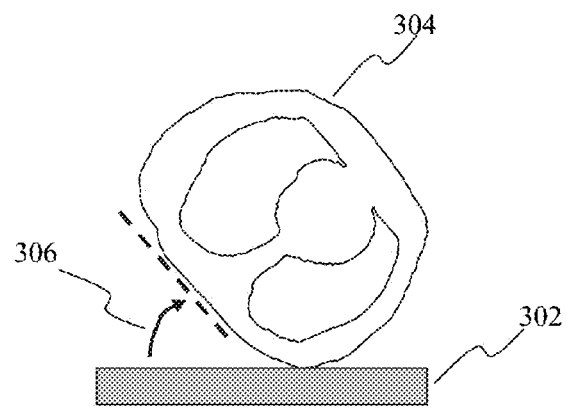
Fig. 3a                  Fig. 3b

METHOD AND SYSTEM FOR ESTIMATING A DEFLATED LUNG SHAPE FOR VIDEO ASSISTED THORACIC SURGERY

CROSS-REFERENCE TO RELATED APPLICATIONS

The present application claims priority to U.S. Provisional Application Ser. No. 62/072,685, filed Oct. 30, 2014, entitled "Methods for the Prediction of a Deflated Lung Model for Video Assisted Thoracic Surgery," which is incorporated herein by reference in its entirety.

BACKGROUND

1. Technical Field

The present teaching relates to surgical procedure assistance. More specifically, the present teaching is directed methods, systems, and programming for estimating a deflated lung shape in video assisted thoracic surgery.

2. Discussion of Technical Background

In minimally invasive thoracic surgery, patients are pre-scanned with a computed tomography (CT) image. Surgical planning is then performed based on the CT images. Three-dimensional (3D) models of anatomical structures may be built from the CT images. Such models may include, but not limited to, models of a 3D lung, a 3D airway, a 3D vessel, a lung lobe fissure, and a tumor. A lesion resection plan may be generated based on the 3D models. A typical resection plan may include where the incision line is, how much safety margin may be put around the tumor, how a critical anatomical structure, such as lung fissures, may be avoided. Quantitative information may include, but not limited to, the distances of the tumor to critical anatomies, distances of the resection surface to critical anatomies, the depth on resection surface from the incision line. Due to its minimally invasive nature, the Video Assisted Thoracic Surgery (VATS) has become widely adopted. During VATS, a tiny video camera and surgical instruments are inserted into the patient's chest. Through looking at the images transmitted to a display monitor, the surgeon performs the procedures, such as lesion resection. At the time of surgery, however, the lung is made collapsed. That is, part of air is let out of the lung. Due to the shape change of the lung, the pre-surgical plan obtained using the pre-operative CT images may no longer be applicable. For example, the distance of the tumor to the lung surface is no longer the same as that computed from pre-surgical planning. On the other hand, it may not be practical to perform another CT scan during the VATS procedure. Therefore, there is a need to provide an improved solution to solve the above-mentioned problems.

SUMMARY

The present teaching relates to surgical procedure assistance. More specifically, the present teaching is directed methods, systems, and programming for estimating a deflated lung shape in video assisted thoracic surgery.

In one example, a method, implemented on a computing device having at least one processor, storage, and a communication platform capable of connecting to a network for surgical procedure assistance is disclosed. A first volume of air inside a lung is obtained based on a first image, e.g., a CT image, of the lung captured prior to a surgical procedure. The lung has a first shape on the first image. A second volume of air deflated from the lung is determined based on a second image, e.g., a video image, of the lung captured during the surgical procedure. A second shape of the lung is estimated based on the first shape of the lung and the first air volume inside the lung and second volume of air deflated from the lung. A surgical plan is updated based on the estimated second shape of the lung.

In a different example, a system for surgical procedure assistance is disclosed. The system includes a total air volume estimation unit, an outflow air volume estimation unit, a deflation unit, and a pre-operative plan transformation unit. The total air volume estimation unit is configured for obtaining a first volume of air inside a lung based on a first image, e.g., a CT image, of the lung captured prior to a surgical procedure. The lung has a first shape on the first image. The outflow air volume estimation unit is configured for obtaining a second volume of air deflated from the lung determined based on a second image, e.g., a video image, of the lung captured during the surgical procedure. The deflation unit is configured for estimating a second shape of the lung based on the first shape of the lung and the first air volume inside the lung and second volume of air deflated from the lung. The pre-operative plan transformation unit is configured for updating a surgical plan based on the estimated second shape of the lung.

Other concepts relate to software for implementing the present teaching on surgical procedure assistance. A software product, in accord with this concept, includes at least one non-transitory machine-readable medium and information carried by the medium. The information carried by the medium may be executable program code data, parameters in association with the executable program code, and/or information related to a user, a request, content, or information related to a social group, etc.

In one example, a non-transitory machine readable medium having information recorded thereon for surgical procedure assistance is disclosed. The recorded information, when read by the machine, causes the machine to perform a series of processes. A first volume of air inside a lung is obtained based on a first image, e.g., a CT image, of the lung captured prior to a surgical procedure. The lung has a first shape on the first image. A second volume of air deflated from the lung is determined based on a second image, e.g., a video image, of the lung captured during the surgical procedure. A second shape of the lung is estimated based on the first shape of the lung and the first air volume inside the lung and second volume of air deflated from the lung. A surgical plan is updated based on the estimated second shape of the lung.

Additional features will be set forth in part in the description which follows, and in part will become apparent to those skilled in the art upon examination of the following and the accompanying drawings or may be learned by production or operation of the examples. The features of the present teachings may be realized and attained by practice or use of various aspects of the methodologies, instrumentalities and combinations set forth in the detailed examples discussed below.

BRIEF DESCRIPTION OF THE DRAWINGS

The methods, systems, and/or programming are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 3a shows an exemplary pre-operative CT image according to one embodiment of the present teaching;

FIG. 3b shows an exemplary patient orientation during VATS according to one embodiment of the present teaching;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, systems, components, and/or circuitry have been described at a relatively high-level, without detail, in order to avoid unnecessarily obscuring aspects of the present teachings.

The present teaching is directed to methods, systems, and programming for estimating a deflated lung shape and for transforming a pre-surgical plan made on images of non-deflated lung. In one example, since it may not be practical to do a CT scan during the VATS procedure, it is highly desirable to make use of the pre-surgical plan to guide the procedure by estimating the lung shape change during VATS. The present teaching discloses a method and system for estimating the shape of a deflated lung from the pre-surgical CT image. With the model of a deflated lung, the pre-operative plan may be adapted to work in the VATS procedure. The system can be realized as a specialized and networked system by utilizing one or more computing devices (e.g., mobile phone, personal computer, etc.) and network communications (wired or wireless). In the following, CT image modality will be used as an exemplary imaging modality. The scope of the present teaching, however, is not limited to the CT imaging modality and can be applied to any known imaging modality such as MRI imaging modality and ultrasound imaging modality.

Figure 1:
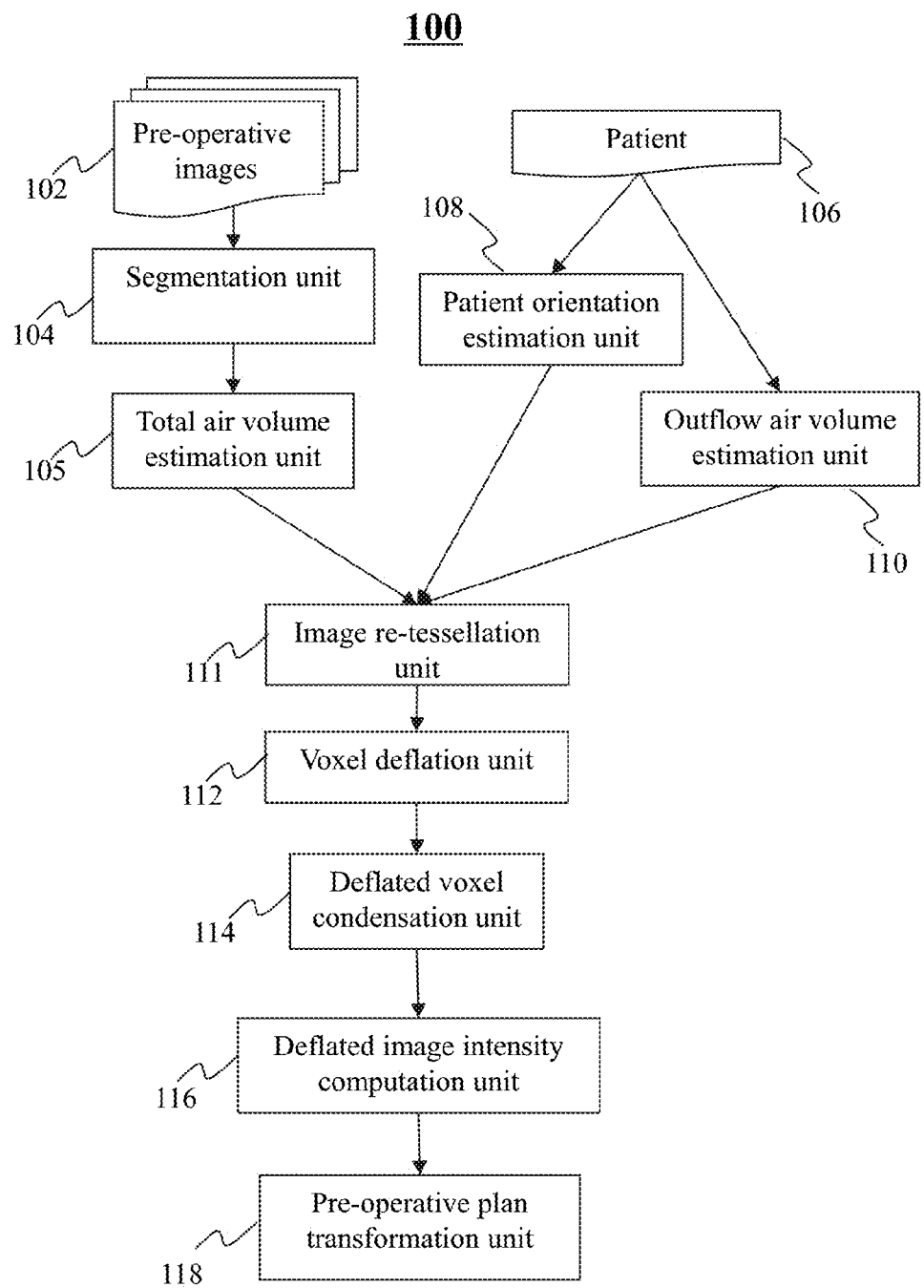
FIG. 1 shows an exemplary system diagram for estimating a deflated lung shape and transforming a pre-operative plan according to one embodiment of the present teaching.

FIG. 1 shows an exemplary system diagram 100 facilitating the estimation of a deflated lung shape and transformation of pre-surgical planning for the deflated lung, according to an embodiment of the present teaching. The system 100 includes a segmentation unit 104 for segmenting a lung from pre-operative CT images 102, a total air volume estimation unit 105, a patient orientation estimation unit 108 for estimating the orientation of a patient 106 during a surgical procedure, e.g., a VATS, an outflow air volume estimation unit 110, an image re-tessellation unit 111, a voxel deflation unit 112, a deflated voxel condensation unit 114, an deflated image intensity computation unit 116, and a pre-operative plan transformation unit 118.

In this embodiment, the total air volume estimation unit 105 estimates the total air volume in the lung from the pre-operative CT images 102. The patient orientation estimation unit 108 estimates the orientation of the patient 106 during the VATS procedure. The outflow air volume estimation unit 110 estimates the air volume that is led out of the lung during the VATS procedure. The image re-tessellation unit 111 re-samples the pre-operative CT images 102 according to the patient orientation information. The voxel deflation unit 112 deflates each re-tessellated voxel in the direction of patient's gravity according to the total air volume in the lung based on the pre-procedural scan and the total outflow air volume during the procedure. The deflated voxel condensation unit 114 condenses the deflated image. The deflated image intensity computation unit 116 computes the intensity of the deflated image. The pre-plan transformation unit 118 maps the pre-operative plan onto the deflated image space and obtains the models of the deflated anatomical structures.

Figure 2:
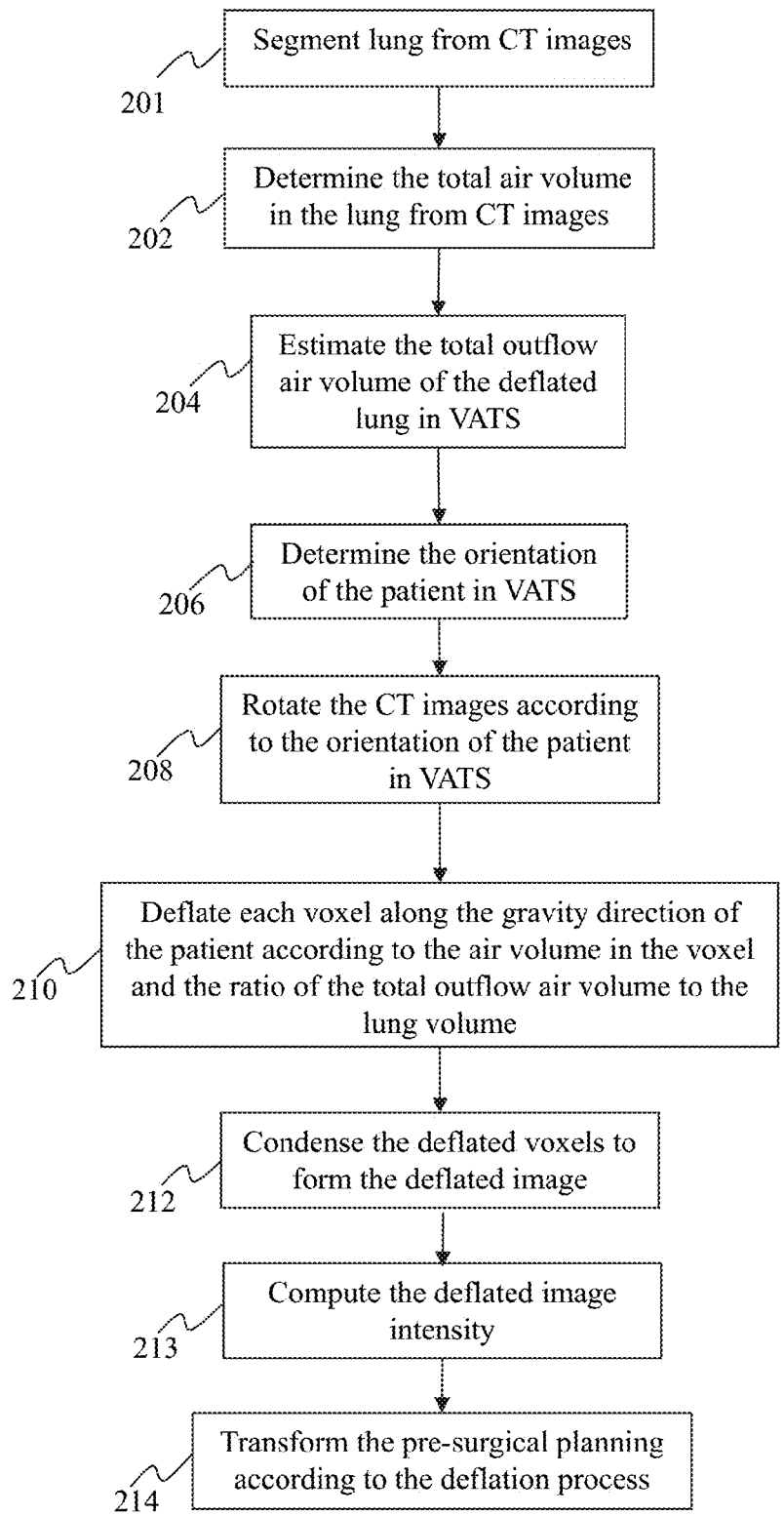
FIG. 2 shows an exemplary flowchart of a process for estimating a deflated lung shape according to one embodiment of the present teaching.

FIG. 2 illustrates an exemplary flowchart for estimating a deflated lung shape, according to one embodiment of the present teaching. At 201, the lung is segmented from the pre-operative CT images. Left lung and right lung may be segmented separately. In the example, only the lung undergoing VATS procedure will be concerned. At 202, the air volume in the lung is estimated. The air volume estimation may be performed for the affected lung during the VATS. Any suitable approaches may be used for the estimation of lung air volume. For example, an approached is disclosed by John Fleming et al in their publication of "Determination of regional lung air volume distribution at mid-tidal breathing from computed tomography: a retrospective study of normal variability and reproducibility", BMC Medical Imaging 2014, 14:25, which is incorporated by reference in its entirety. At 204, the outflow air volume for the deflated lung may be estimated. In one example, the estimation may be done by visually inspecting the chest cavity air space of the patient during the VATS as the percentage of the lung volume based on video images transmitted from the inside the lung cavity. In another example, the air outflow air volume may be estimated automatically by integrating the deflation of each voxel as shown in 210 below. Details of the integrated estimation of air volume will be described later in this disclosure.

At 206, the patient orientation during the VATS is estimated. Since the pre-operative CT image is usually taken in the supine position, whereas the patient during the VATS may be in any other position, such as the prone position, or the oblique position. Suppose that the pre-surgical CT images were taken at the supine position, the angle of the patient's rotation from the supine position to the surgical position may be estimated. FIG. 3 illustrates the angle of rotation from a supine position to an oblique position. FIG. 3a is a pre-operative CT lung image, and FIG. 3b shows the patient in the surgical position, e.g., the oblique position in this example. In FIG. 3b, 302 is the surgical table, 304 is the patient body, and 306 is the angle of the patient body 304's rotation from the supine view. The angle of rotation 306 may be estimated manually by visual inspect, or automatically. In one example, sensors, such as electro-magnetic position tracking sensors, may be attached on the patient's skin. The positions of the sensors may be first recorded in the supine position of the patient. Then when the patient is re-positioned to the surgical position during the VATS, the sensor positions are recorded and compared to the sensor positions in the supine position of the patient. The angle of rotation may be computed from the positional change of the sensors. For example, a rigid transformation model may be used to fit the sensor position data to compute the angle of rotation.

Figure 4A:
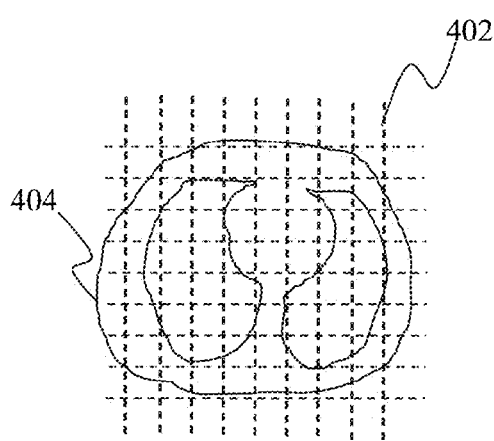
FIG. 4a shows an exemplary image pixels as grids according to one embodiment of the present teaching.
Figure 4B:
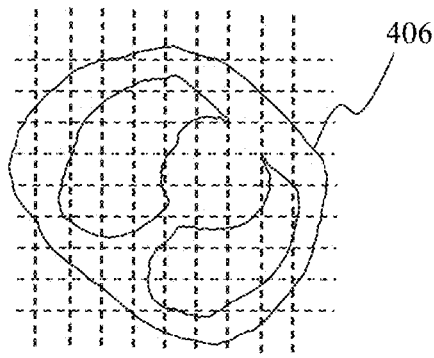
FIG. 4b illustrates exemplary rotation of the image in FIG. 4a according to one embodiment of the present teaching.

At 208, the pre-operative CT image data may be rotated to match the orientation of the patient in the VATS. Then the rotated image may be re-tessellated, e.g., in finer grids, in the vertical direction. For example, each voxel may be tessellated into 10 sub-voxels in the direction of the patient gravity, which is the vertical direction. FIG. 4 illustrates examples of the rotation and tessellation operations. FIG. 4a shows the original voxels (shown as grids 402) on the pre-operative patient image 404. FIG. 4b shows the rotated image 406 to match the orientation of the patient in the VATS procedure.

Figure 5A:
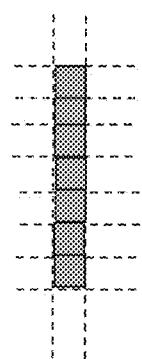
FIG. 5a shows an exemplary column of voxels according to one embodiment of the present teaching.
Figure 5B:
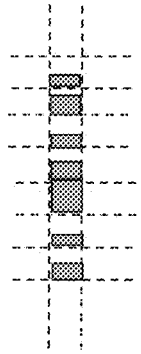
FIG. 5b illustrates exemplary deflation of the voxels shown in FIG. 5a according to one embodiment of the present teaching.
Figure 5C:
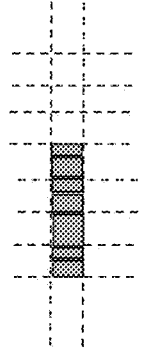
FIG. 5c shows exemplary condensation of the deflated voxels shown in FIG. 5b in the vertical down-ward direction according to one embodiment of the present teaching.

At 210, each voxel in the VATS image space is deflated in the vertical and downward direction in the re-tessellated image space. First, the air volume contained in each voxel may be estimated, e.g., based on the method in John Fleming et al, "Determination of regional lung air volume distribution at mid-tidal breathing from computed tomography: a retrospective study of normal variability and reproducibility", BMC Medical Imaging 2014, 14:25. The outflow air volume in each voxel may then be computed as the product of the air volume in the voxel and the ratio of the total outflow air volume in the lung to the total lung volume. The air volume in the voxel may depend on the type of tissue represented by the voxel. As an example, if a voxel is from a blood vessel, the air estimation in that voxel may be given a zero-milliliter air in that voxel, and thus the voxel may not be deflated. Then the deflated voxel volume may be computed as the original voxel volume minus the deflated air volume. Since the voxel is deflated in the gravity direction, the deflated voxel dimension in the horizontal plane may be kept the same as that before deflation, and the deflated voxel height may be computed as the original height minus the equivalent height of the air part. The equivalent height of the air part may be computed as the remaining air volume divided by the voxel area in the horizontal plane. In the CT image, the voxel area in the horizontal plane is the product of the voxel size in the column and depth directions in the CT image space. At 212, after the voxels are deflated, they may need to be condensed in the gravity direction (which is downward). That is, the deflated voxel will be packed together to remove the gaps caused by the out-let air. FIG. 5 illustrates an example of the voxel deflation process. FIG. 5a represents a column of voxels, FIG. 5b shows the deflated column of voxels, and FIG. 5c shows the condensed and deflated column of voxels. After the condensation, each voxel in the original image space may be a combination of more than one pixel.

At 213, the pixel intensity of the condensed voxel may be computed. Since each condensed voxel may be a combination of multiple deflated voxels (or a fraction), the intensity of each deflated voxel may be first computed. This may be based on the air left in the voxel. In CT imaging, the intensity (Hounsfield unit) had been calibrated such that 100% air corresponds to an intensity of −1000, and 0% air corresponds to an intensity of 0 or above. The deflated voxel intensity may be linearly interpolated based on the air percentage in the voxel. Then the voxel intensity of condensed voxel may be computed as the average of the deflated voxels contained in the condensed voxel. In one example, the estimated shape of the deflated lung is then obtained based on the intensities of each condensed and deflated voxel of the original images.

At 214, the pre-surgical plan is transformed according to deflation processes above. For example, the resection plan, such as the cutting surface, may be transformed according to the underlying transformation in the deflation process.

As one example of 204, the outflow air volume estimation may be combined with a digital deflation process. First the coordinates of the incision point for inserting a video camera in the VATS may be estimated. The estimation may be performed by performing a 3D reconstruction of the patient skin surface (e.g., by a laser scanner) and register the reconstructed surface with the skin surface in the pre-surgical CT image, so that after registration any point on the patient skin surface during VATS may be mapped to find the corresponding point in the skin surface of the CT image. A simulated virtual camera may then be placed in the CT image space in the same position and orientation as the actual video camera during the VATS. The position and orientation of the actual video camera may be found in terms of electro-magnetic tracking device. A simulated image may be generated based on a pre-segmented chest wall and the pre-segmented lung. Then the lung may be digitally deflated as a function of one deflation control parameter. This deflation control parameter may be the ratio of the outflow air volume to the lung volume. As the deflation control parameter gradually decreases from 1.0, the rendered image from the virtual camera for the digitally deflated lung may be matched against the actual video image of the patient during the VATS. The best match will determine the deflation control parameter, and thus the outflow air volume.

As another example of 204, the outflow air volume may be estimated based on video image processing of a laparoscopic camera. A laparoscope usually includes 2 stereo cameras. From the stereo images, some image features, such as edges, linear structures, and points, which correspond to the chest cavity and deflected lung surface may be extracted. These features may be matched across the stereo images and then used to reconstruct the 3D coordinates of such structures in the camera space. These 3D structures may be used to find the surface of the chest cavity and the lung surface by interpolation. The air volume may be calculated as the enclosure of the interpolated surface.

To implement various modules, units, and their functionalities described in the present disclosure, computer hardware platforms may be used as the hardware platform(s) for one or more of the elements described herein (e.g., the system 100 described with respect to FIGS. 1-5). The hardware elements, operating systems and programming languages of such computers are conventional in nature, and it is presumed that those skilled in the art are adequately familiar therewith to adapt those technologies to surgical assistance as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 6:
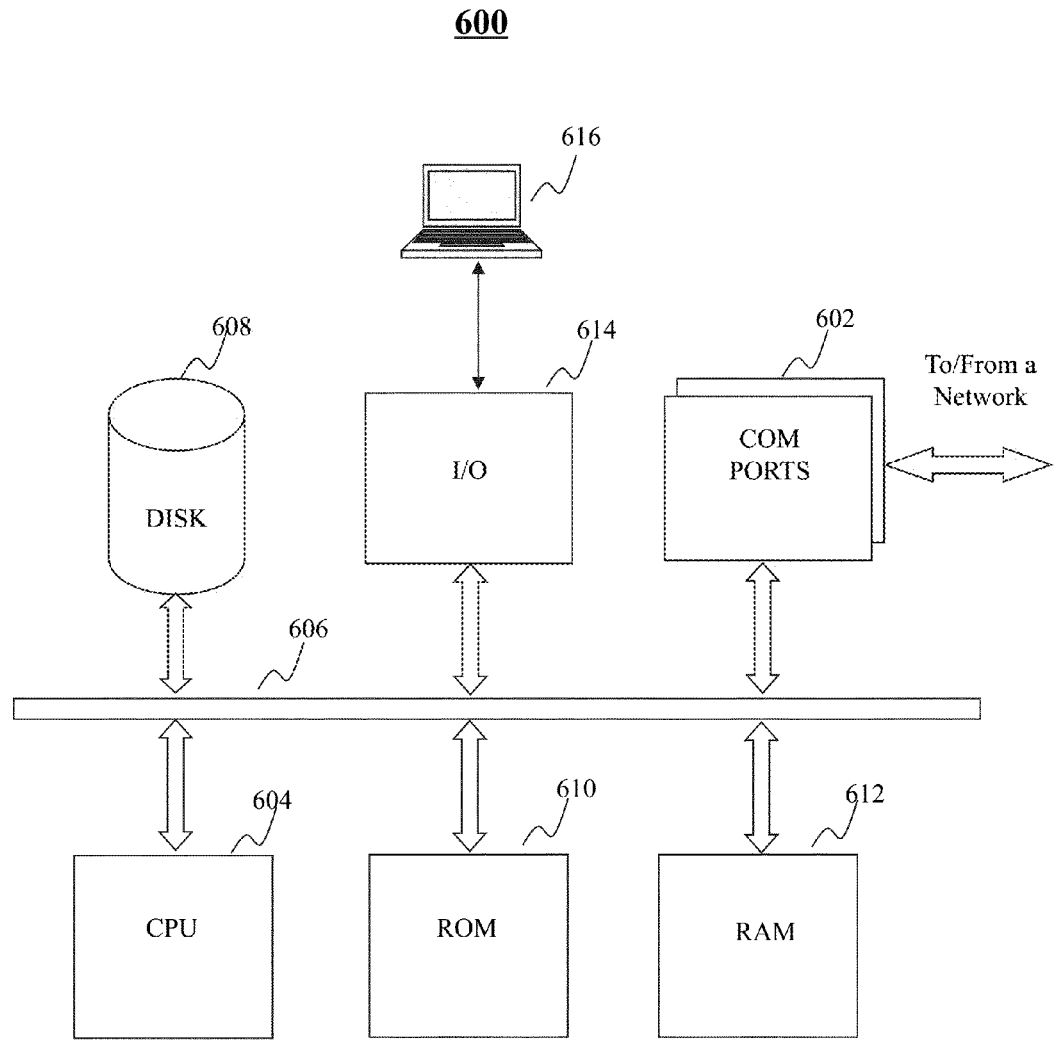
FIG. 6 depicts the architecture of a computer which can be used to implement a specialized system incorporating the present teaching.

FIG. 6 depicts the architecture of a computing device which can be used to realize a specialized system implementing the present teaching. Such a specialized system incorporating the present teaching has a functional block diagram illustration of a hardware platform which includes user interface elements. The computer may be a general purpose computer or a special purpose computer. Both can be used to implement a specialized system for the present teaching. This computer 600 may be used to implement any component of surgical assistance techniques, as described herein. For example, the system 100 may be implemented on a computer such as computer 600, via its hardware, software program, firmware, or a combination thereof. Although only one such computer is shown, for convenience, the computer functions relating to surgical assistance as described herein may be implemented in a distributed fashion on a number of similar platforms, to distribute the processing load.

The computer 600, for example, includes COM ports 602 connected to and from a network connected thereto to facilitate data communications. The computer 600 also includes a central processing unit (CPU) 604, in the form of one or more processors, for executing program instructions. The exemplary computer platform includes an internal communication bus 606, program storage and data storage of different forms, e.g., disk 608, read only memory (ROM) 610, or random access memory (RAM) 612, for various data files to be processed and/or communicated by the computer, as well as possibly program instructions to be executed by the CPU 604. The computer 600 also includes an I/O component 614, supporting input/output flows between the computer and other components therein such as user interface elements 616. The computer 600 may also receive programming and data via network communications.

Hence, aspects of the methods of surgical assistance and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer into the hardware platform(s) of a computing environment or other system implementing a computing environment or similar functionalities in connection with surgical assistance. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer-readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the surgical assistance system as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method, implemented on a computing device having at least one processor, storage, and a communication platform capable of connecting to a network for surgical procedure assistance, comprising:

obtaining a first volume of air inside a lung based on a first image of the lung captured prior to a surgical procedure, wherein the lung has a first shape on the first image;

capturing a video image of the lung during the surgical procedure;

computing, via registering the captured video image with the first image, a second volume of air deflated from the lung;

estimating a second shape of the lung based on the first shape of the lung, the first air volume inside the lung, and the second volume of air deflated from the lung, the second shape being estimated by condensing a plurality of voxels in the first image along a gravity direction; and updating a surgical plan based on the estimated second shape of the lung.

2. The method of claim 1, wherein the surgical procedure includes a video assisted thoracic surgery (VATS), and the first image includes a computed tomography (CT) image.

3. The method of claim 1, further comprising:
obtaining an angle of rotation of the lung from a first position at which the first image was captured to a second position at which the video image was captured; and
adjusting the first shape of the lung on the first image based on the angle of rotation, wherein the second shape of the lung is estimated based on the adjusted first shape of the lung, the first volume, and the second volume.

4. The method of claim 1, wherein computing the second volume of the air comprises:
obtaining at least the video image having the lung and surrounding structures;
extracting features from at least the video image;
reconstructing three dimensional (3D) coordinates of the lung and the surrounding structures based on the features; and
estimating a third volume of space between the lung and the surrounding structures based on the 3D coordinates.

5. The method of claim 1, wherein computing the second volume of the air comprises:
estimating a plurality of simulated second shapes of the lung as a function of a deflation control parameter;
determining one of the plurality of simulated second shapes of the lung based on the video image of the lung; and
determining the deflation control parameter associated with the determined simulated second shape of the lung.

6. The method of claim 1, wherein estimating the second shape of the lung comprises:
calculating a third volume of air inside the lung during the surgical procedure based on the second volume; and
determining a ratio between the first volume and the third volume.

7. The method of claim 6, wherein estimating the second shape of the lung further comprises:
estimating, for each voxel of the plurality of voxels included in the first shape of the lung on the first image, the first volume of air inside each voxel based on an intensity of each voxel;
calculating the second volume of air inside each voxel based on the first volume of air inside the voxel and the ratio; and
condensing the plurality of voxels along the gravity direction based on the second volume of air inside each voxel.

8. A system for surgical procedure assistance, comprising:
at least one processor configured to:
obtain a first volume of air inside a lung based on a first image of the lung captured prior to a surgical procedure, wherein the lung has a first shape on the first image;
capture a video image of the lung during the surgical procedure;
compute, via registering the captured video image with the first image, a second volume of air deflated from the lung;
estimate a second shape of the lung based on the first shape of the lung, the first air volume inside the lung, and the second volume of air deflated from the lung, the second shape being estimated by condensing a plurality of voxels in the first image along a gravity direction; and
update a surgical plan based on the estimated second shape of the lung.

9. The system of claim 8, wherein the surgical procedure includes a video assisted thoracic surgery (VATS), and the first image includes a computed tomography (CT) image.

10. The system of claim 8, wherein the at least one processor is further configured to:
obtain an angle of rotation of the lung from a first position at which the first image was captured to a second position at which the video image was captured; and
adjust the first shape of the lung on the first image based on the angle of rotation, wherein the second shape of the lung is estimated based on the adjusted first shape of the lung, the first volume, and the second volume.

11. The system of claim 8, wherein the at least one processor is further configured to:
obtain at least the video image having the lung and surrounding structures;
extract features from at least the video image;
reconstruct three dimensional (3D) coordinates of the lung and the surrounding structures based on the features; and
estimate a third volume of space between the lung and the surrounding structures based on the 3D coordinates.

12. The system of claim 8, wherein the at least one processor is further configured to:
estimate a plurality of simulated second shapes of the lung as a function of a deflation control parameter;
determine one of the plurality of simulated second shapes of the lung based on the video image of the lung; and
determine the deflation control parameter associated with the determined simulated second shape of the lung.

13. The system of claim 8, wherein the at least one processor is further configured to:
calculate a third volume of air inside the lung during the surgical procedure based on the second volume; and
determine a ratio between the first volume and the third volume.

14. The system of claim 13, wherein the at least one processor is further configured to:
estimate, for each voxel of the plurality of voxels included in the first shape of the lung on the first image, the first volume of air inside each voxel based on an intensity of each voxel;
calculate the second volume of air inside each voxel based on the first volume of air inside the voxel and the ratio; and
condense the plurality of voxels along the gravity direction based on the second volume of air inside each voxel.

15. A non-transitory machine readable medium having information recorded thereon for surgical procedure assistance, wherein the information, when read by a machine, causes the machine to perform the steps of:
obtaining a first volume of air inside a lung based on a first image of the lung captured prior to a surgical procedure, wherein the lung has a first shape on the first image;
capturing a video image of the lung during the surgical procedure;
computing, via registering the captured video image with the first image, a second volume of air deflated from the lung;
estimating a second shape of the lung based on the first shape of the lung, the first air volume inside the lung, and the second volume of air deflated from the lung, the second shape being estimated by condensing a plurality of voxels in the first image along a gravity direction; and updating a surgical plan based on the estimated second shape of the lung.

16. The medium of claim 15, wherein the surgical procedure includes a video assisted thoracic surgery (VATS), and the first image includes a computed tomography (CT) image.

17. The medium of claim 15, wherein the information, when read by the machine, causes the machine to further perform the steps of:
   obtaining an angle of rotation of the lung from a first position at which the first image was captured to a second position at which the video image was captured; and
   adjusting the first shape of the lung on the first image based on the angle of rotation, wherein the second shape of the lung is estimated based on the adjusted first shape of the lung, the first volume, and the second volume.

18. The medium of claim 15, wherein computing the second volume of the air comprises:
   obtaining at least the video image having the lung and surrounding structures;
   extracting features from at least the video image;
   reconstructing three dimensional (3D) coordinates of the lung and the surrounding structures based on the features; and
   estimating a third volume of space between the lung and the surrounding structures based on the 3D coordinates.

19. The medium of claim 15, wherein computing the second volume of the air comprises:
   estimating a plurality of simulated second shapes of the lung as a function of a deflation control parameter;
   determining one of the plurality of simulated second shapes of the lung based on the video image of the lung; and
   determining the deflation control parameter associated with the determined simulated second shape of the lung.

20. The medium of claim 15, wherein estimating the second shape of the lung comprises:
   calculating a third volume of air inside the lung during the surgical procedure based on the second volume; and
   determining a ratio between the first volume and the third volume.

21. The medium of claim 20, wherein estimating the second shape of the lung further comprises:
   estimating, for each voxel of the plurality of voxels included in the first shape of the lung on the first image, the first volume of air inside each voxel based on an intensity of each voxel;
   calculating the second volume of air inside each voxel based on the first volume of air inside the voxel and the ratio; and
   condensing the plurality of voxels along the gravity direction based on the second volume of air inside each voxel.

* * * * *